(12) United States Patent
Kim et al.

(10) Patent No.: US 9,410,942 B2
(45) Date of Patent: Aug. 9, 2016

(54) TEST APPARATUS WITH DETECTOR THAT ROTATES IN ALIGNMENT WITH MICROFLUIDIC DEVICE AND CONTROL METHOD THEREOF

(71) Applicant: SAMSUNG ELECTRONICS CO., LTD., Suwon-si (KR)

(72) Inventors: Dong Young Kim, Daegu (KR); Jin Beom Hong, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 824 days.

(21) Appl. No.: 13/692,459

(22) Filed: Dec. 3, 2012

(65) Prior Publication Data

US 2013/0143327 A1 Jun. 6, 2013

(30) Foreign Application Priority Data

Dec. 5, 2011 (KR) ........................ 10-2011-0129080

(51) Int. Cl.
*G01N 35/00* (2006.01)
*G01N 21/07* (2006.01)
*G01N 33/50* (2006.01)
*B01L 3/00* (2006.01)

(52) U.S. Cl.
CPC ............ *G01N 33/50* (2013.01); *B01L 3/50273* (2013.01); *G01N 35/00069* (2013.01); *B01L 2200/025* (2013.01); *B01L 2300/022* (2013.01); *B01L 2300/023* (2013.01); *B01L 2300/0803* (2013.01); *B01L 2300/126* (2013.01); *B01L 2400/0409* (2013.01); *G01N 21/07* (2013.01); *Y10T 436/11* (2015.01); *Y10T 436/111666* (2015.01)

(58) Field of Classification Search
None
See application file for complete search history.

(56) References Cited

U.S. PATENT DOCUMENTS

| | | | |
|---|---|---|---|
| 2005/0175332 A1* | 8/2005 | Shigeura | B01J 19/0093 392/418 |
| 2006/0205581 A1* | 9/2006 | Chammas | A61M 1/3693 494/16 |
| 2009/0253130 A1* | 10/2009 | Yoo | B01F 13/0059 435/6.11 |
| 2010/0060886 A1* | 3/2010 | Hwang | G01J 1/08 356/225 |
| 2010/0245815 A1* | 9/2010 | Ducree | B01L 3/502707 356/246 |

FOREIGN PATENT DOCUMENTS

KR 1020080022018 A 3/2008
KR 1020100030400 A 3/2010

* cited by examiner

*Primary Examiner* — Yelena G Gakh
*Assistant Examiner* — Michelle Adams
(74) *Attorney, Agent, or Firm* — Sughrue Mion, PLLC

(57) ABSTRACT

A test apparatus in which detectors and objects to be detected are rotated at the same speed, and a control method thereof are provided. The test apparatus includes a rotation driving unit that includes a rotary shaft; a microfluidic device that is loaded on the rotary shaft and includes at least one object to be detected; a rotating member that is mounted on the rotary shaft and includes at least one detector to detect the objects of the microfluidic device; and a controller configured to operate the rotation driving unit such that the microfluidic device and the rotating member are rotated at the same speed on the rotary shaft.

13 Claims, 6 Drawing Sheets

TEST APPARATUS WITH DETECTOR THAT ROTATES IN ALIGNMENT WITH MICROFLUIDIC DEVICE AND CONTROL METHOD THEREOF

CROSS-REFERENCE TO RELATED APPLICATION

This application claims priority from Korean Patent Application No. 10-2011-0129080, filed on Dec. 5, 2011 in the Korean Intellectual Property Office, the disclosure of which is incorporated herein by reference.

BACKGROUND

1. Field

Apparatuses and methods consistent with exemplary embodiments relate to a test apparatus which performs testing of bio-molecules through a microfluidic device, such as a bio-disc.

2. Description of the Related Art

A microfluidic device used to analyze or test bio-molecules includes objects, such as chambers or sheets of test paper to detect a material to be analyzed or tested.

A test apparatus includes detectors, such as cameras or optical sensors to detect the objects to be detected of the microfluidic device, and thus detects results of biochemical reactions occurring within the objects to be detected.

In order to allow the detector to detect the presence of, or the concentration of, the material to be analyzed or tested by detecting the result of the biochemical reaction occurring within a rotating microfluidic device, it is required that the object to be detected be moved to a detection region which is able to be reached by the detector. As such, additional time is required to move the object to be detected to the detection region.

SUMMARY

Exemplary embodiments provide a test apparatus in which detectors and objects to be detected are rotated at the same speed, and a control method thereof.

In accordance with an aspect of an exemplary embodiment, there is provided a test apparatus for detecting objects to be detected in a microfluidic device, the test apparatus including a rotation driving unit having a rotary shaft for rotating the microfluidic device, a rotating member mounted on the rotary shaft and having disposed thereon one or more detectors to detect the objects to be detected of the microfluidic device, and a controller configured to operate the rotation driving unit such that the microfluidic device and the rotating member are rotated at the same speed on the same rotary shaft.

The controller may be configured to align the objects to be detected of the microfluidic device and the detectors of the rotating member, when the microfluidic device is loaded.

The controller may be configured to operate the detectors to detect the objects to be detected when the rotation driving unit is operated, and to receive results of detection transmitted from the detectors.

The controller and the detectors may communicate with each other via a wired communication method or a wireless communication method, which includes near field communication (NFC), BLUETOOTH, ZIGBEE, Wi-Fi, radio frequency identification (RFID), and universal serial bus (USB).

The rotating member may include a printed circuit board (PCB) on which the detectors are mounted.

The detectors may receive power supplied through a slip ring mounted on the rotary shaft.

The detectors may receive power supplied from a power generation device mounted on the rotary shaft of the rotation driving unit.

The power generation device may include coils mounted on the rotary shaft and fixed magnets surrounding the coils.

The detectors may receive power supplied from a power supply unit wirelessly.

The detectors may include cameras and optical sensors.

In accordance with an aspect of another exemplary embodiment, there is provided a control method of a test apparatus. The method includes aligning objects to be detected of a microfluidic device with detectors of the test apparatus, and operating a rotation driving unit such that the objects to be detected and the detectors are rotated in alignment with each other at the same speed.

The detectors may be installed on a rotating member mounted on a rotary shaft of the rotation driving unit.

The control method may further include operating the detectors to detect the objects to be detected, when the rotation driving unit is operated.

Aligning the objects to be detected and the detectors of the microfluidic device and the detectors to detect the objects to be the detectors may include positioning the objects to be detected of the microfluidic device and the detectors opposite each other.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
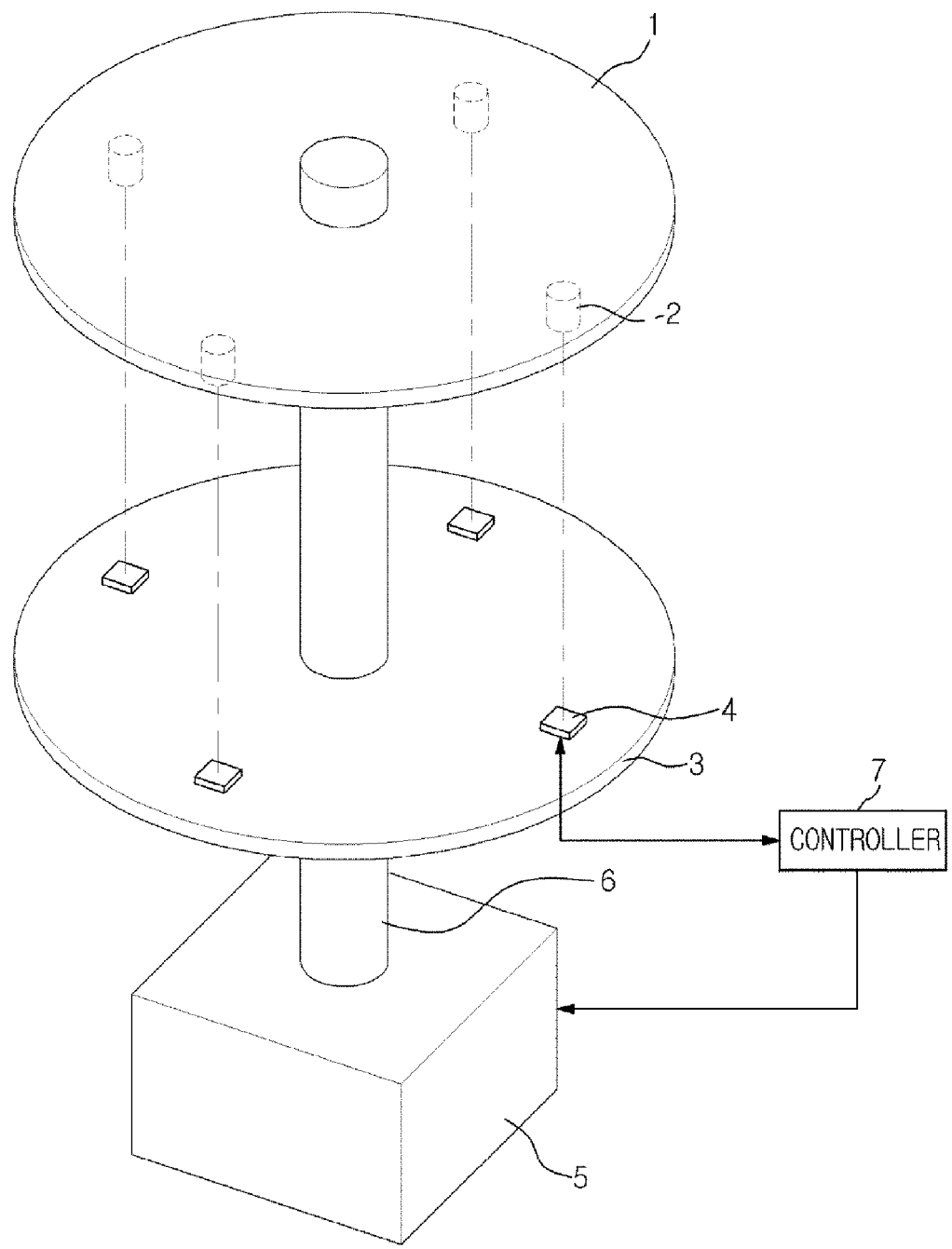
FIG. 1 is a schematic view illustrating the configuration of a test apparatus in accordance with an exemplary embodiment.

Reference will now be made in detail to exemplary embodiments, examples of which are illustrated in the accompanying drawings, wherein like reference numerals refer to like elements throughout.

Figure 2:
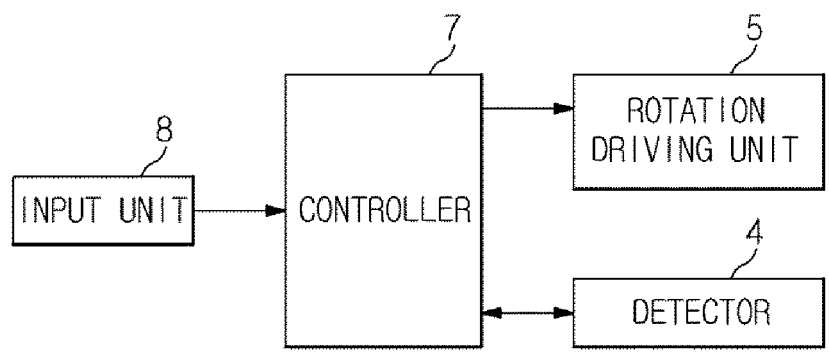
FIG. 2 is a block diagram illustrating the configuration of the test apparatus in accordance with an exemplary embodiment.
Figure 3:
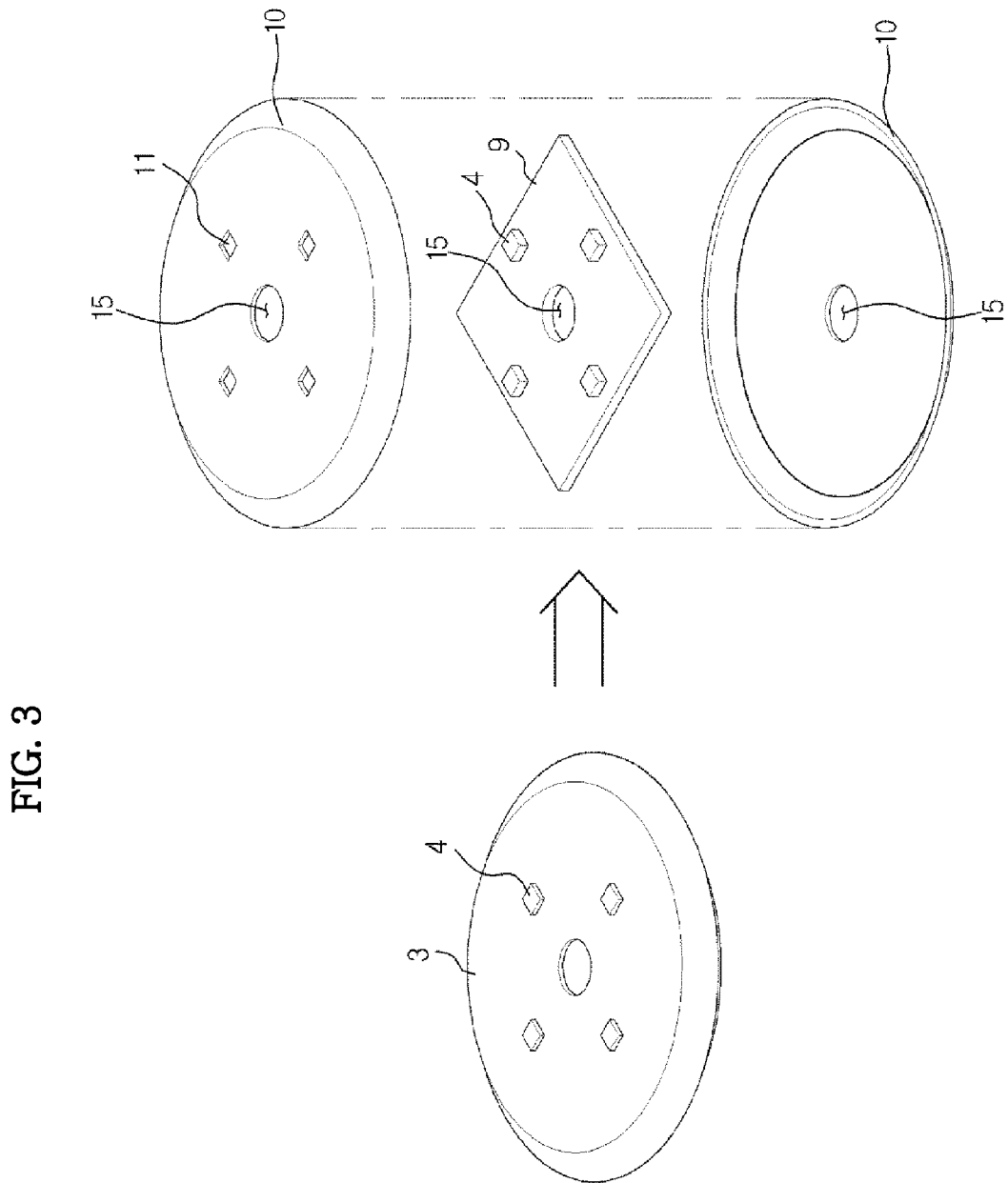
FIG. 3 is a view illustrating the configuration of a rotating member in accordance with an exemplary embodiment.

FIG. 1 is a schematic view illustrating the configuration of a test apparatus in accordance with an exemplary embodiment, FIG. 2 is a block diagram illustrating the configuration of the test apparatus in accordance with the exemplary embodiment, and FIG. 3 is a view illustrating the configuration of a rotating member in accordance with the exemplary embodiment.

The test apparatus in accordance with the exemplary embodiment includes a rotation driving unit 5 supplying rotating force, a rotating member 3 mounted on a rotary shaft 6 of the rotation driving unit 5 and provided with detectors 4 to detect objects 2 within a microfluidic device 1.

The test apparatus executes analysis and testing of various biochemical materials. Various kinds of test apparatuses may be provided according to types of sample to be analyzed.

Exemplary samples may include, but are not limited to, DNA, oligo-nucleotides, RNA, PNA, ligand, receptors, antigens, antibodies, milk, urine, saliva, hairs, crop samples, meat samples, fowl samples, livestock samples, processed food samples, oral cells, tissue samples, semen, proteins and other bio-molecules.

Further, materials to be analyzed may include, but are not limited to, proteins, antigens, antibodies, DNA, RNA, oligonucleotides and receptors. For example, if urine is used as a sample, analysis of blood, glucose, ascorbic acid, ketones, proteins, sugars, urobilinogen, or bilirubin may be performed.

The rotation driving unit 5 rotates or stops the microfluidic device 1 and the rotating member 3. Within the microfluidic device 1, samples or reagents contained therein may move or be mixed using centrifugal force generated due to rotation as driving pressure.

The rotation driving unit 5 may include a motor drive device (not shown) controlling the angular position of a rotating body. For example, the motor drive device may employ a stepper motor or a DC motor.

The rotation driving unit 5 includes a motor generating rotating force, and the rotary shaft 6 providing the rotating force.

The rotating member 3 provided with the detectors 4 is mounted on the rotary shaft 6 of the rotation driving unit 5.

The microfluidic device 1 includes the objects 2 therein to be detected. As used herein, objects 2 to be detected may include chambers within the microfluidic device, or sheets of test paper mounted on or in the microfluidic device, in which a material to be analyzed or a material to be tested is received and a biochemical reaction to detect such a material occurs.

The presence or concentration of the material to be analyzed/tested may be confirmed by detecting results of the biochemical reaction to detect the material within the microfluidic device.

The detectors 4 detect the results of the biochemical reaction occurring in the objects 2 to be detected. For example, a level of light emission, color development or fluorescence may provide information to confirm the presence or concentration of the material to be analyzed or tested.

Examples of the detectors 4 include, but are not limited to, charge-coupled device (CCD), complementary metal-oxide semiconductor (CMOS) camera modules, and/oror optical sensors to detect the level of light emission or fluorescence. That is, the detectors 4 may employ any device which may detect the results of the biochemical reaction to detect the material to be analyzed or tested.

The rotating member 3 may include a printed circuit board 9 on which the detectors 4 may be installed. Although this exemplary embodiment illustrates the rotating member 3 as having a disc shape the same as or similar to the shape of the microfluidic device 1, the rotating member 3 may have any shape which provides a region in which the detectors 4 may be installed, and which is configured to be rotatably installed on the rotary shaft 6.

With reference to FIG. 3, the rotating member 3 may include a printed circuit board 9 on which the detectors 4 are installed, and housings 10 provided above and below the printed circuit board 9 and connected to each other, so that the printed circuit board 9 is interposed the housings 10.

Through holes 15, through which the rotating member 3 is mounted on the rotary shaft 6, may be formed through centers of the printed circuit board 9 and each of the housings 10.

Further, detector holes 11, through which the detectors 4 protrude or are exposed to the outside, may be formed on the upper housing 10 at positions corresponding to the detectors 4.

The housings 10 may be formed of a material configured to reduce noise or vibration generated by rotation of the rotating member 3.

The rotating member 3 may be stabilized by supporting members having various known structures and shapes so as to avoid movements other than rotation, i.e., to ensure that the rotating member 3 is not vertically shaken or tilted during rotation.

At least one detector 4 may be installed on the rotating member 3. The number of and/or the positions of the installed detectors 4 may be determined in relation to the structure of the microfluidic device 1.

When the microfluidic device 1 is loaded or installed on the test apparatus and the rotation driving unit 5 is operated, the microfluidic device 1 and the rotating member 3 are rotated at the same speed. Therefore, when the detectors 4 and the objects 2 to be detected are aligned at corresponding positions of the same radius, the microfluidic device 1 and the rotating member 3 are rotated at the same speed, and thus the detectors 4 may continuously detect variation of the objects 2 to be detected in real time.

A controller 7 receives instructions through an input unit 8 of the test apparatus, and adjusts operation of the rotation driving unit 5 and the detectors 4.

When the microfluidic device 1 is loaded into the test apparatus, the controller 7 outputs an operation signal to operate the rotation driving unit 5. When the rotation driving unit 5 is operated, the controller 7 operates the detectors 4 to detect any variations generated in the objects 2 to be detected of the microfluidic device 1. If the detectors 4 are camera modules, the detectors 4 photograph any variations and transmit the variation to the controller 7. If the detectors 4 are optical sensors, the detectors 4 sense the intensity of light and transmit the intensity to the controller 7.

The controller 7 may communicate with the detectors 4 using a wireless communication method. Since the detectors 4 detect variation generated in the objects 2 to be detected of the microfluidic device 1 while rotating at the same speed of the objects 2 to be detected, a wireless communication method rather than a wired communication method may be used although a wired communication method may be used as well. Exemplary communication methods include, but are not limited to, near field communication (NFC), BLUETOOTH, ZIGBEE, Wi-Fi, radio frequency identification (RFID), and universal serial bus (USB).

When the microfluidic device 1 is loaded into the test apparatus, the controller 7 aligns the objects 2 to be detected of the microfluidic device 1 and the detectors 4 installed on the rotating member 3. For example, the controller 7 may operate the rotation driving unit 5 so as to align the detectors 4 with the objects 2 to be detected of the microfluidic device 1, before the microfluidic device 1 is loaded and is connected to the rotary shaft 6.

Various methods may be used for aligning the objects 2 to be detected of the microfluidic device 1 and the detectors 4 installed on the rotating member 3. The controller 7 may automatically align the objects 2 to be detected and the detectors 4, as described above, or such alignment may be designed in advance. For example, the microfluidic device 1 may include a designated reference mark and a corresponding structure within the test apparatus, such as a tray on which the microfluidic device 1 is loaded, may also have a designated reference mark, such that the objects 2 to be detected and the detectors 4 are aligned if the marks coincide with each other when the microfluidic device 1 is loaded. Of course, in addition to the above-described methods, various known methods may be used to align the objects 2 to be detected and the detectors 4.

The controller 7 receives results of detection from the detectors 4 and thus confirms presence of, or the concentration of, the material to be analyzed or tested.

Figure 4:
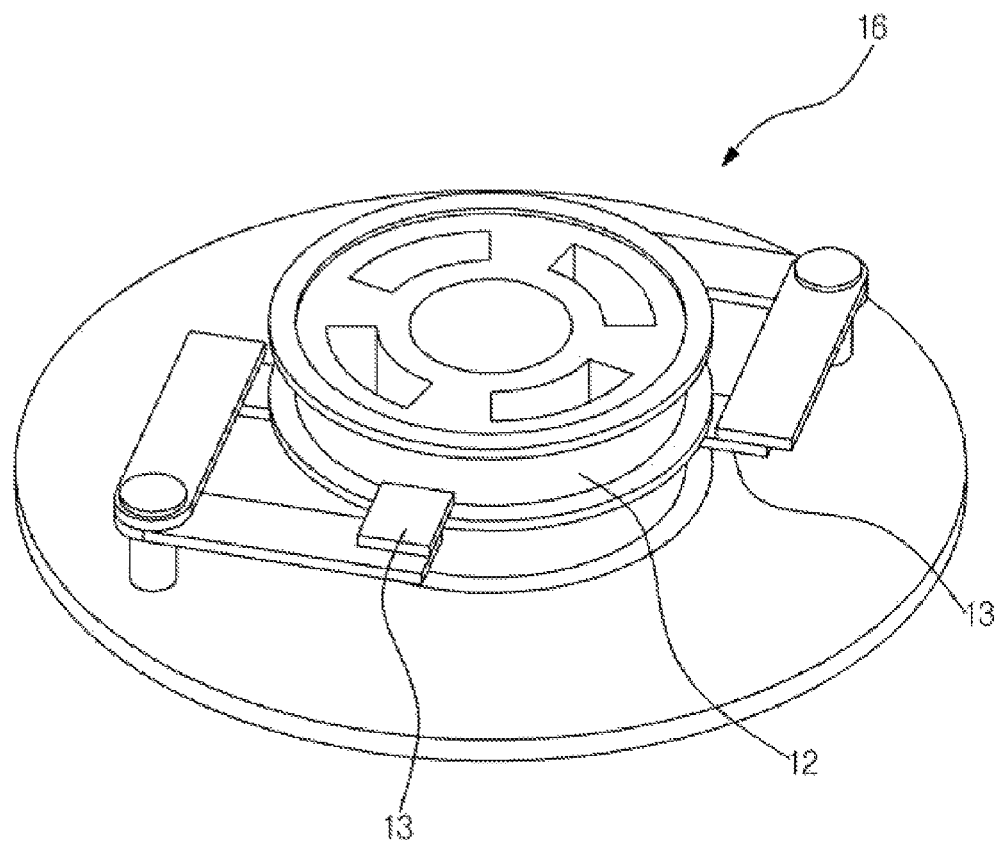
FIG. 4 is a view illustrating a slip ring to supply power to detectors of the test apparatus in accordance with an exemplary embodiment.
Figure 5:
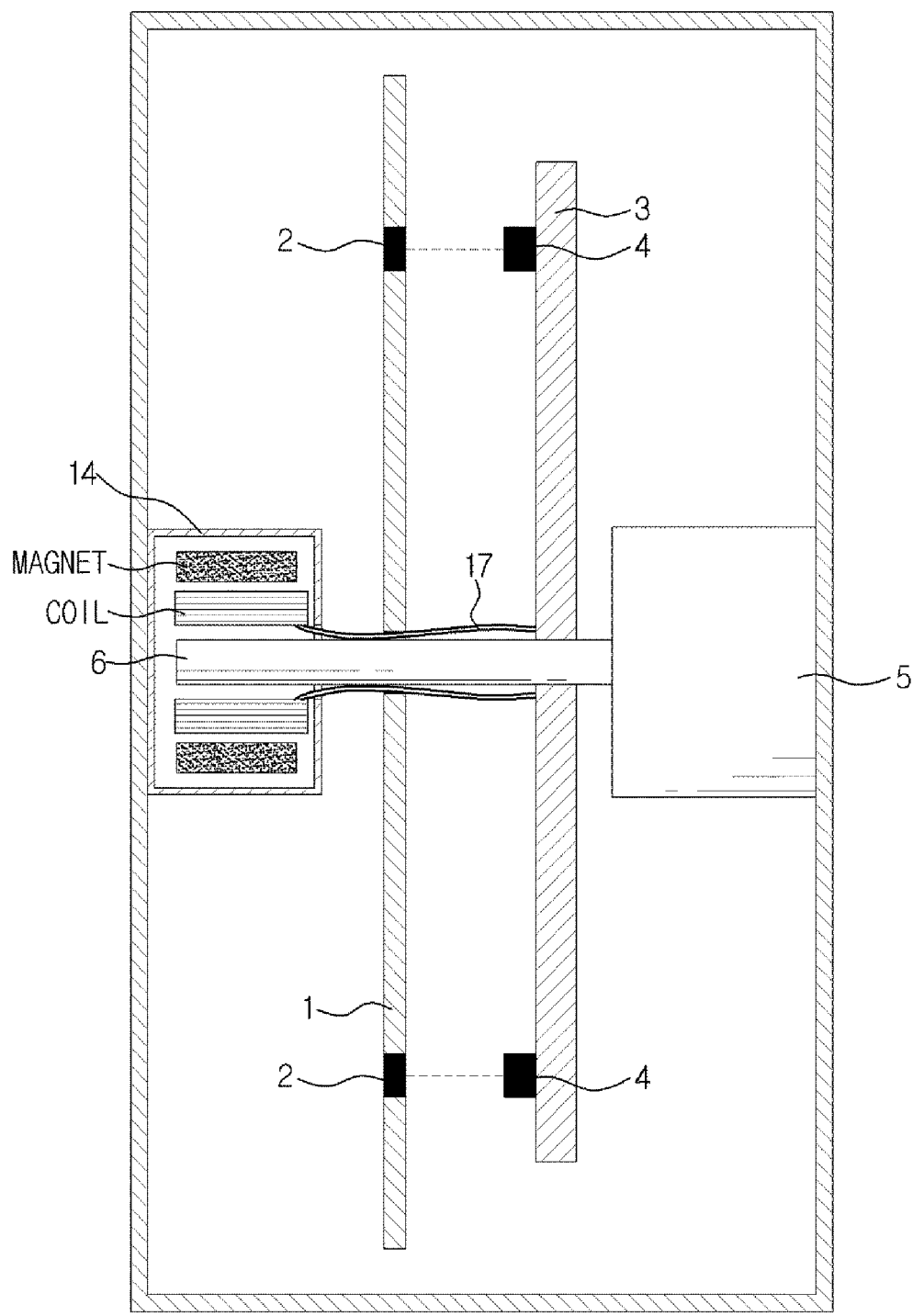
FIG. 5 is a view illustrating a power generation device to supply power to the detectors of the test apparatus in accordance with an exemplary embodiment.

FIG. 4 is a view illustrating a slip ring 16 to supply power to the detectors 4 of the test apparatus in accordance with the exemplary embodiment, and FIG. 5 is a view illustrating a power generation device to supply power to the detectors 4 of the test apparatus in accordance with the exemplary embodiment.

In general, if power needs to be supplied to a rotating object and/or a rotating object operates another apparatus, the slip ring 16 may be installed to supply power. For example, a contact slip ring transmitting power or a signal may include a ring 12 and brushes 13.

Exemplary contact slip rings for use in the test apparatus may be divided into brush types, which are mainly used in power transmission, or wire types, which reduce generation of contact resistance or noise in signal transmission at high-speed rotation, etc.

FIG. 4 illustrates the slip ring 16 as a brush-type contact slip ring which supplies power to the detectors 4 installed on the rotating member 3.

FIG. 5 is a view illustrating supply of power to the detectors 4 through a power generation device 14 using the same principle of a conventional alternator.

The rotary shaft 6 is connected to the power generation device 14 and rotates coils of the power generation device 14. When the coils disposed between magnets are rotated, current flows in a direction based on Fleming's right-hand law.

Such current is supplied to the detectors 4 along wires 17 connected to the rotating member 3, thereby operating the detectors 4.

If the detectors 4 are powered by DC power, rectifiers (not shown) may be provided so as to convert AC power supplied to the detectors 4 into DC power.

Accordingly, power may be supplied to the rotating detectors 4 using the above-described slip ring 16 and power generation device 14. In addition to such a configuration for supplying power to the detectors 4, a method of wirelessly supplying power from a main power supply to the detectors 4 may be used.

Since supply of power to a rotating object via wires may cause structural restriction, if power is wirelessly supplied to a rotating object from a main power Wireless power transmission technology may include any one or more of various transmission methods, depending on transmission distances. In the exemplary embodiment described herein, power transmission may be executed through a short-distance low-output transmission method. Short-distance transmission technology transmits energy within the range of several meters may be used to transmit comparatively low output power based on radiation of electromagnetic waves, which is well suited to transmission of power to the rotating detectors 4.

Otherwise, non-radiative middle-distance wireless energy transmission technology may be used to efficiently transmit power. Such technology uses the near field effect for transmission within a short distance in accordance with the frequency/wavelength used, and coincides the resonance frequencies at transmission/reception units with each other.

Figure 6:
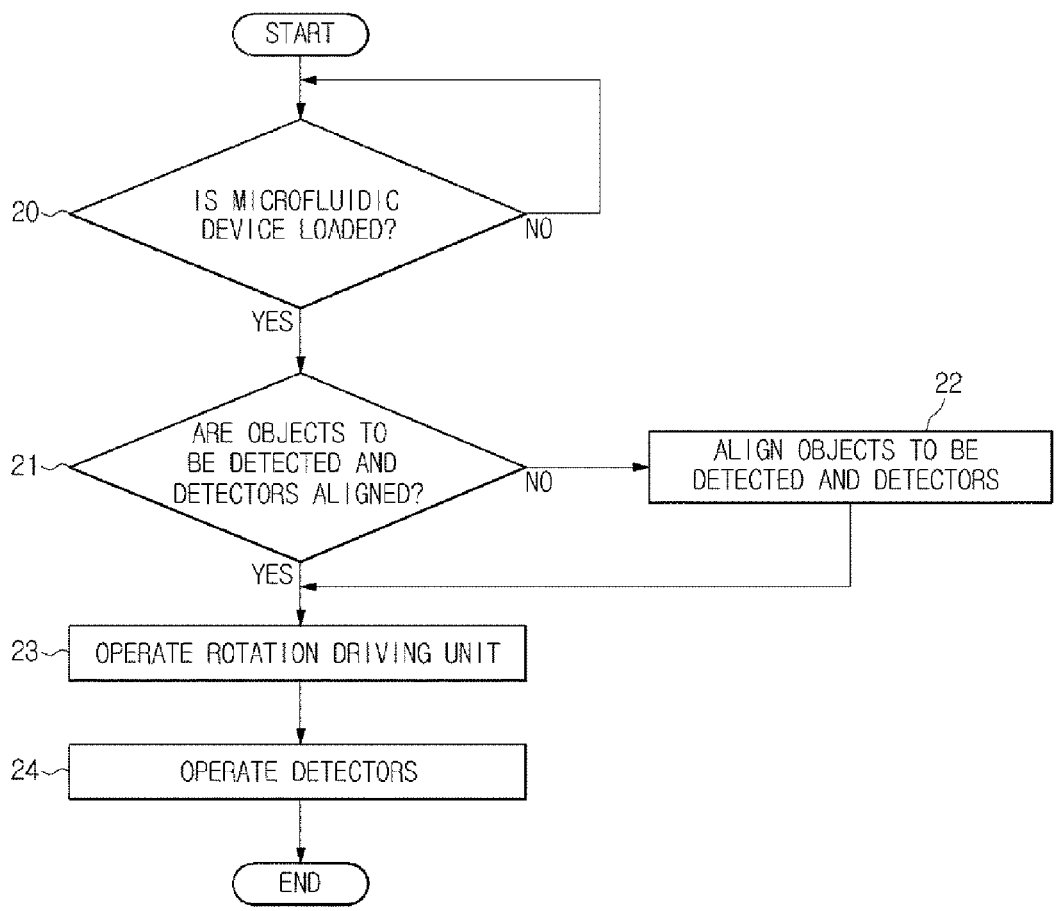
FIG. 6 is a flowchart illustrating a control method of the test apparatus in accordance with an exemplary embodiment.

FIG. 6 is a flowchart illustrating a control method of the test apparatus in accordance with the exemplary embodiment.

With reference to FIG. 6, the controller 7 determines whether or not the microfluidic device 1 is loaded into the test apparatus (Operation 20).

If it is determined that the microfluidic device 1 is loaded, the controller 7 determines whether or not the objects 2 to be detected of the microfluidic device 1 and the detectors 4 installed on the rotating member 3 are aligned (Operation 21).

If it is determined that the objects 2 to be detected and the detectors 4 are not aligned, the controller 7 aligns the objects 2 to be detected and the detectors 4 (Operation 22).

When the objects 2 to be detected and the detectors 4 are aligned, the controller 7 operates the rotation driving unit 5 (Operation 23).

When the rotation driving unit 5 is operated, the rotating member 3 installed on the rotary shaft 6 and the microfluidic device 1 loaded on the rotary shaft 6 rotate at the same speed. That is, the objects 2 to be detected and the detectors 4 are rotated at the same speed once they are opposite each other.

When the rotation driving unit 5 is operated, the controller 7 operates the detectors 4 to detect any variations generated within the objects 2 to be detected (Operation 24).

Since the objects 2 to be detected and the detectors 4 are rotated at the same speed when they are opposite each other, the detectors 4 may continuously detect variations generated in the objects 2 to be detected in real time.

As is apparent from the above description, in a test apparatus and a control method thereof in accordance with exemplary embodiments, the detectors execute detection of the objects 2 to be detected during rotation, and thus continuously detect variation generated in the objects to be detected in real time.

Further, the objects to be detected and the detectors are rotated together, thus solving problems caused by positional errors generated due to rotation of the objects to be detected only.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. A test apparatus comprising:
    a microfluidic device configured to be loaded on a rotary shaft of a rotation driving unit
    and comprising an object in which a material to be tested by the test apparatus is received;
    the rotation driving unit, which is configured to rotate the microfluidic device when the microfluidic device is loaded on the rotary shaft;
    a rotating member that is directly mounted on the rotary shaft of the rotation driving unit and includes at least one detector to detect the object of the microfluidic device; and
    a controller configured to operate the rotation driving unit such that the microfluidic device and the rotating member are rotated at the same speed on the rotary shaft.

2. The test apparatus according to claim 1, wherein:
    the controller is further configured to operate the at least one detector to detect the object when the rotation driving unit is operated, and to receive results of detection transmitted from the detector.

3. The test apparatus according to claim 2, wherein the controller and the at least one detector communicate with each other via wired communication or wireless communication.

4. The test apparatus according to claim 3, wherein the wired or wireless communication is selected from the group consisting of near field communication (NFC), BLUETOOTH, ZIGBEE, Wi-Fi, radio frequency identification (RFID), and universal serial bus (USB).

5. The test apparatus according to claim 1, wherein the rotating member includes a printed circuit board (PCB) on which the at least one detector is mounted.

6. The test apparatus according to claim 1, further comprising a slip ring that is mounted on the rotary shaft and supplies power to the at least one detector.

7. The test apparatus according to claim 1, further comprising a power generation device that is mounted on the rotary shaft of the rotation driving unit and supplies power to the at least one detector.

8. The test apparatus according to claim 7, wherein the power generation device comprises coils mounted on the rotary shaft and fixed magnets surrounding the coils.

9. The test apparatus according to claim 1, wherein the at least one detector receives power supplied from a power supply unit wirelessly.

10. The test apparatus according to claim 1, wherein the at least one detector comprises at least one of a camera and an optical sensor.

11. A control method of the test apparatus of claim 1, the method comprising:
    loading the microfluidic device on the rotary shaft of the rotation driving unit;
    aligning the object of the microfluidic device with the at least one detector; and
    operating the rotation driving unit such that the object and the at least one detector are rotated in alignment with each other at the same speed.

12. The control method according to claim 11, further comprising operating the at least one detector to detect the object when the rotation driving unit is operated.

13. The control method according to claim 11, wherein the aligning the object with the at least one detector includes positioning the object and the at least one detector opposite each other.

* * * * *